US012409257B2

(12) United States Patent
Friedberg et al.

(10) Patent No.: US 12,409,257 B2
(45) Date of Patent: Sep. 9, 2025

(54) PERITONEAL OXYGENATION SYSTEM AND METHOD

(71) Applicants: University of Maryland, Baltimore, Baltimore, MD (US); University of Maryland, College Park, College Park, MD (US)

(72) Inventors: Joseph Friedberg, Baltimore, MD (US); Hosam Fathy, Kensington, MD (US); Jin-Oh Hahn, Potomac, MD (US); Mahsa Doosthosseini, Laurel, MD (US); Majid Aroom, Preston, MD (US); Kevin Aroom, Silver Spring, MD (US)

(73) Assignees: UNIVERSITY OF MARYLAND, BALTIMORE, Baltimore, MD (US); UNIVERSITY OF MARYLAND, COLLEGE PARK, College Park, MD (US)

( * ) Notice: Subject to any disclaimer, the term of this patent is extended or adjusted under 35 U.S.C. 154(b) by 1054 days.

(21) Appl. No.: 17/308,567

(22) Filed: May 5, 2021

(65) Prior Publication Data
US 2021/0346582 A1    Nov. 11, 2021

Related U.S. Application Data

(60) Provisional application No. 63/020,207, filed on May 5, 2020.

(51) Int. Cl.
*A61M 1/28* (2006.01)
*A61M 1/32* (2006.01)
*A61M 1/36* (2006.01)

(52) U.S. Cl.
CPC .............. *A61M 1/28* (2013.01); *A61M 1/282* (2014.02); *A61M 1/32* (2013.01); *A61M 1/369* (2013.01);
(Continued)

(58) Field of Classification Search
CPC ........ A61M 1/28; A61M 1/282; A61M 1/285; A61M 1/32; A61M 1/369;
(Continued)

(56) References Cited

U.S. PATENT DOCUMENTS 4,661,092 A * 4/1987 Popovich .............. A61M 1/281
514/672
2016/0271311 A1 * 9/2016 Matheis .............. A61M 1/1698

FOREIGN PATENT DOCUMENTS

WO    WO-2020018567 A1 *  1/2020

OTHER PUBLICATIONS

Tawfic, Qutaiba A. and Rajini Kausalya. "Liquid Ventilation." Oman Medical Journal (2011) vol. 26, No. 1: 4-9.
(Continued)

*Primary Examiner* — Shefali D Patel
(74) *Attorney, Agent, or Firm* — Whiteford, Taylor & Preston, LLP; Gregory M. Stone

(57) ABSTRACT

Systems and methods for gas exchange in a patient are provided that use an external circuit to cause oxygenation perfusion in a body cavity (such as an abdomen) of the patient using an inert chemical (e.g., perfluorocarbon), independent of lungs. The external circuit includes components configured to control properties of the chemical, including temperature, flow rate, pressure, oxygenation percentage, and carbon dioxide percentage. The systems also include safety features to reduce a likelihood of injury to the patient. Each of the safety features and the properties of the chemical can be controlled by a healthcare worker, such as a physician, a nurse, or an emergency operator, for a particular patient.

20 Claims, 4 Drawing Sheets

(52) U.S. Cl.
CPC .............. *A61M 2202/0476* (2013.01); *A61M 2210/1017* (2013.01); *A61M 2210/1021* (2013.01)

(58) Field of Classification Search
CPC .. A61M 2202/0021; A61M 2202/0476; A61M 2205/33; A61M 2205/3368; A61M 2205/36; A61M 2205/50; A61M 2210/1017; A61M 2210/1021
See application file for complete search history.

(56) References Cited

OTHER PUBLICATIONS

Wolfson, Marla R. and Thomas H. Shaffer. "Liquid ventilation: an adjunct for respiratory management." Pediatric Anesthesia 2004 14:15-23.
Wolfson, Marla R. and Thomas H. Shaffer. "Pulmonary applications of perfluorochemical liquids: Ventilation and beyond." Pediatric Respiratory Reviews (2005) 6, 117-127.
Anzueto, Antonio, et al. "Incidence, risk factors and outcome of barotrauma in mechanically ventilated patients." Intensive Care Med (2004) 30:612-619.
Boussarsar, Mohamed, et al. "Relationship between ventilatory settings and barotrauma in the acute respiratory distress syndrome." Intensive Care Med (2002) 28:406-413.
Carr, Shamus R., et al. "Peritoneal perfusion with oxygenated perfluorocarbon augments systemic oxygenation." Chest 2006;130;402-411.
Castro, Camila Irene and Juan Carlos Briceno. "Perfluorocarbon-Based Oxygen Carriers: Review of Products and Trials." Artificial Organs. 34(8):622-634. 2010.
Cohn, Claudia S. and Melissa M. Cushing. "Oxygen Therapeutics: Perfluorocarbons and Blood Substitute Safety." Critical Care Clinics vol. 25, Issue 2. 2009: 399-414.
Curtis, Scott E., et al. "Cardiac output during liquid (perfluorocarbon) breathing in newborn piglets." Critical Care Medicine. vol. 19, No. 2. 1991.
Eworuke, Efe, et al. "National incidence rates for Acute Respiratory Distress Syndrome (ARDS) and ARDS cause-specific factors in the United States (2006-2014)." Journal of Cricial Care 47 (2018) 192-197.
Faithfull, N.S., et al. "Gas Exchange During Peritoneal Perfusion with Perfluorocarbon Emulsions." Advances in Experimental Medicine and Biology (1985) 191:463-472.
Faithfull, N.S., et al. "Whole Body Oxygenation Using Intraperitoneal Perfusion of Fluorocarbons." Br. J. Anaesth. (1984), 56, 867.
Fiala, Andrea, et al. "Treatment of a Rat Model of LPS-Induced ARDS via Peritoneal Perfusion of Oxygen Microbubbles." Journal of Surgical Research. Feb. 2020 (246) 450-456.
Filho, Ivo P. Torres. "Mini-Review: Perfluorocarbons, Oxygen Transport, and Microcirculation in Low Flow States: In Vivo and In Vitro Studies." Shock. vol. 52, Supplement 1, pp. 19-27, 2019.
Gammon, R. Bruce, et al. "Pulmonary Barotrauma in Mechanical Ventilation Patterns and Risk Factors." Chest vol. 102, No. 2 Aug. 1992.
Ghaffari, Azad. "dSPACE and Real-Time Interface in Simulink." Department of Electrical and Computer Engineering. San Diego State University. 2012.
Greenspan, Jay S., et al. "Liquid Ventilation." Seminars in Perinatology, vol. 24 No. 6 (Dec.), 2000: pp. 396-405.
Hatoum, Liana. "Diffusion Modeling and Device Development for Peritoneal Membrane Oxygenation." (2016). Mechanical (and Materials) Engineering—Dissertations, Theses, and Student Research. 96.
Hill, Steven E. "Perfluorocarbons: Knowledge Gained From Clinical Trials." Shock, vol. 52, Supplement 1, pp. 60-64, 2019.

Hirschl, Ronald B., et al. "Initial Experience with Partial Liquid Ventilation in Adult Patients With the Acute Respiratory Distress Syndrome." JAMA, Feb. 7, 1996—vol. 275, No. 5.
Hirschl, Ronald B., et al. "Prospective, Randomized, Controlled Pilot Study of Partial Liquid Ventilation in Adult Acute Respiratory Distress Syndrome." American Journal of Respiratory and Critical Care Medicine vol. 165 2002.
Jahr, Jonathan S., et al. "Blood Substitutes and Oxygen Therapeutics: A Review." Anesthesia & Analgesia. Jan. 2021, vol. 132, No. 1.
Kandler, Michael A., et al. "Persistent Improvement of Gas Exchange and Lung Mechanics by Aerosolized Perfluorocarbon." American Journal of Respiratory and Critical Care Medicine vol. 164 2001. 31-35.
Leach, Corinne Lowe, et al. "Partial Liquid Ventilation with Perflubron in Premature Infants with Severe Respiratory Distress Syndrome." The New England Journal of Medicine. vol. 335, No. 11. 1996.
Lee, Sungsoo, et al. "Transpleural perfusion with oxygenated perfluorocarbon increases systemic oxygenation." Respirology (2009) 14, 695-700.
Legband, Nathan, et al. "Preliminary Evaluation of the Viability of Peritoneal Drainage Catheters Implanted in Rats for Extended Durations." J Invest Surg. Jun. 2019 ; 32(4): 321-330.
Legband, Nathan. "Development of Peritoneal Microbubble Oxygenation as an Extrapulmonary Treatment for Hypoxia." (2017). Mechanical (and Materials) Engineering—Dissertations, Theses, and Student Research. 115.
Marasco, Silvana F. "Review of ECMO (Extra Corporeal Membrane Oxygenation) Support in Critically Ill Adult Patients." Heart, Lung and Circulation 2008; 17S:S41-S47.
Matsutani, Noriyuki, et al. "Efficacy of Peritoneal Oxygenation Using a Novel Artificial Oxygen Carrier (TRM-645) in a Rat Respiratory Insufficiency Model." Surg Today (2010) 40:4.
Matsutani, Noriyuki, et al. "The Peritoneum as a Novel Oxygenation Organ: Revitalization of Intraperitoneal Oxygenation." Shock, vol. 30, No. 3, pp. 250Y253, 2008.
Mishra, Vinod, et al. "Cost of extracorporeal membrane oxygenation: evidence from the Rikshospitalet University Hospital, Oslo, Norway." European Journal of Cardio-thoracic Surgery 37 (2010) 339-342.
Miyaguchi, Naoyuki, et al. "Transintestinal Systemic Oxygenation Using Perfluorocarbon." Surg Today (2006) 36:262-266.
Murphy, Deirdre A., et al. "Extracorporeal Membrane Oxygenation-Hemostatic Complications." Transfusion Medicine Reviews 29 (2015) 90-101.
O'Grady, Brian J., et al. "A Customizable, Low-Cost Perfusion System for Sustaining Tissue Constructs." SLAS Technology 2018, vol. 23(6) 592-598.
Ohara, Makoto, et al. "Peritoneal lavage with oxygenated perfluorochemical preserves intestinal mucosal barrier function after ischemia-reperfusion and ameliorates lung injury." Crit Care Med 2001 vol. 29. No. 4, 782-788.
Okumara, Shinya, et al. "Liver Graft Preservation Using Perfluorocarbon Improves the Outcomes of Simulated Donation After Cardiac Death Liver Transplantation in Rats." Liver Transplantation 23 1171-1185 2017.
Oxygen Carrier State of the Science Meeting. Combat Casualty Care Research Program (CCCRP) | Feb. 6-8, 2017 | Fort Detrick.
Peyman, Gholam, et al. "Perfluorocarbon Liquids in Ophthalmology." Survey of Ophthalmology. vol. 39 No. 5 Mar.-Apr. 1995.
Potnuru, Devendra, et al. "Design and implementation methodology for rapid control prototyping of closed loop speed control for BLDC motor." Journal of Electrical Systems and Information Technology 5 (2018) 99-111.
Saito, Takaaki, et al. "Intraperitoneal Administration of Hyperbarically Oxygenated Perfluorochemical Enhances Preservation of Intestinal Mucosa Against Ischemia/Reperfusion Injury." Shock, vol. 26, No. 6, pp. 620Y624, 2006.
Sakai, T., et al. "Intraperitoneal Injection of Oxygenated Perfluorochemical Improves the Outcome of Intraportal Islet Transplantation in a Rat Model." Transplantation Proceedings, 38, 3289-3292 (2006).
Sarkar, Suman, et al. "Liquid ventilation." Anesthesia: Essays and Researches; 8(3); Sep.-Dec. 2014.

(56) References Cited

OTHER PUBLICATIONS

Schmidt, John A., et al. "Peritoneal Oxygenation of Normoxic and Hypoxic Dogs." XXXV Trans Am Soc Artif Intern Organs 1989. 35-39.

Shinzeki, Makoto, et al. "Intraperitoneal Administration of Oxygenated Perfluorochemical Inhibits Bacterial Translocation Associated with Severe Acute Pancreatitis." Kobe J. Med. Sci., vol. 49, No. 1, pp. 17-24, 2003.

Spiess, Bruce D. "Perfluorocarbon emulsions as a promising technology: a review of tissue and vascular gas dynamics." J Appl Physiol 106: 1444-1452, 2009.

Spiess, Bruce D. "Perfluorocarbon Gas Transport: An Overview of Medical History With Yet Unrealized Potentials." Shock, vol. 52, Supplement 1, pp. 7-12, 2019.

Spiess, Bruce D. and R.P. Cochran. "Perfluorocarbon Emulsions and Cardiopulmonary Bypass: A Technique for the Future." Journal of Cardiothoracic and Vascular Aneesthesia, vol. 10, No. 1 (Jan.), 1996, pp. 83-90.

Staffey, Kimberly S., et al. "Liquid ventilation with perfluorocarbons facilitates resumption of spontaneous circulation in a swine cardiac arrest model." Resuscitation (2008) 78, 77-84.

Bialas, Christopher, et al. "Artificial oxygen carriers and red blood cell substitutes: A historic overview and recent developments toward military and clinical relevance." J. Trauma Acute Care Surg vol. 87, No. 1, Supplement Jul. 1, 2019.

Biro, George O and Pierre Blais. "Perfluorocarbon Blood Substitutes." CRC Critical Reviews in Oncology/Hematology. vol. 6, Issue 4. 1987.

Cullis, Brett, et al. "Peritoneal Dialysis for Acute Kidney Injury." Peritoneal Dialysis International, vol. 34, pp. 494-517 Jul. 2014.

Hirschl, Ronald B., et al. "Partial Liquid Ventilation in Adult Patients with Ards A Multicenter Phase I-II Trial." Annals of Surgery Vo. 228, No. 5, 692-700. Nov. 1998.

Riess, Jean G. "Understanding the Fundamentals of Perfluorocarbons and Perfluorocarbon Emulsions Relevant to In Vivo Oxygen Delivery." Artificial Cells, Blood Substitutes, and Biotechnology, 33:1, 47-63 2005.

* cited by examiner

PERITONEAL OXYGENATION SYSTEM AND METHOD

CROSS-REFERENCE TO RELATED APPLICATIONS

This application claims the benefit of U.S. Provisional Application No. 63/020,207 titled "Peritoneal Oxygenation System," filed May 5, 2020, which application is incorporated herein by reference in its entirety.

GOVERNMENT LICENSE RIGHTS

This invention was made with government support under Grant Numbers 2031245 and 2031251 awarded by the National Science Foundation. The government has certain rights in the invention.

FIELD OF THE INVENTION

The present invention relates generally to systems and methods for blood oxygenation, and more particularly to systems and methods for providing oxygenation to a patient using the perfusion of an oxygenated perfluorocarbon through the patient's abdominal cavity or other well-vascularized cavities.

BACKGROUND

Respiration consists of two processes: oxygenation and ventilation (carbon dioxide removal). Oxygen, taken in through the lungs, is a necessary component for the chemical reactions that generate the energy of life. The carbon dioxide produced in that reaction must be expelled through the lungs in order to maintain the necessary acid-base balance for enzymatic function and electrolyte homeostasis. The gas exchange takes place in the terminal air sacs of the lungs, the alveoli, which are surrounded by a rich capillary network that permits the diffusion of these gases into or out of the body. The diffusion of both gases is gradient driven, but there is a fundamental difference between these processes. Oxygenation is facilitated by red blood cells and their hemoglobin-mediated, highly evolved mechanisms for oxygen capture/dissociation. In contrast, carbon dioxide is simply dissolved in the bloodstream and cleared by purely gradient driven diffusion across the alveolar capillary membranes.

When a patient is suffering from pulmonary failure, physicians view and treat oxygenation and ventilation as separate processes. While deficits in oxygenation can be augmented either through mechanical ventilation or by providing a higher concentration of inspired oxygen, little can be done to facilitate carbon dioxide clearance without mechanical assistance—simply increasing the amount of air moving in an out of the lungs over a given period of time. When either the oxygen demand exceeds what can be delivered by increasing the inspired oxygen concentration, or carbon dioxide is accumulating to detrimental levels, physicians resort to mechanical ventilation, typically by intubating the airway and placing the patient on a positive pressure mechanical ventilator.

Mechanical ventilation is a critical component in the treatment of patients suffering from pulmonary insufficiency from any cause. This spans the spectrum from nonpulmonary conditions that can affect the lungs, like congestive heart failure, to infections of the lungs, like COVID-19. Any condition resulting in the need to supplement the patient's ability to exchange one or both gases will require mechanical ventilation. Unfortunately, oxygen toxicity and/or barotrauma from mechanical ventilation can actually injure the lungs, either compounding the underlying problem or inducing a second mechanism of pulmonary pathology and dysfunction. This is called ventilator-induced lung injury. Once such injury occurs, the patient is at increased risk from a destructive positive feedback loop where higher levels of support further damages the lungs, necessitating even higher levels of support, which further damages the lungs, until the level of support that can be provided by the ventilator is no longer compatible with life. In such situations, an emergency need arises for more drastic interventions, including the direct oxygenation of the blood using techniques such as extracorporeal membrane oxygenation (ECMO). Unfortunately, ECMO is an extremely scarce resource. Even when available, ECMO is accompanied by limitations/complications that make it inappropriate for many patients. Consequently, the majority of patients who exceed the support achievable with mechanical ventilation do not have other options and will not survive.

Thus, there remains a need in the art for safe and effective pulmonary-independent respiratory support for patients with respiratory failure, and more particularly for systems and methods for pulmonary-independent respiratory support that are capable of providing oxygenation and carbon dioxide clearance, that augment mechanical ventilation, that help rest the lungs, and that avoid the costs, complexities, and contraindications associated with ECMO.

SUMMARY OF THE INVENTION

Disclosed herein are systems and methods for an extracorporeal ventilator that uses the surfaces of a patient's abdominal cavity, and more particularly the peritoneal membrane, for gas exchange. Systems and methods employed in accordance with certain aspects of the invention use the abdominal cavity as essentially a substitute lung for gas exchange, and are thus capable of providing needed gas exchange when the patient has reached the limits of mechanical ventilator support, and which may at early stages of mechanical ventilation offer a prophylactic measure to lower the risk of ventilator-induced lung injury.

In accordance with certain aspects of an embodiment of the invention, a system for supplementing gas exchange in a patient uses an external circuit to cause oxygenation perfusion in a patient's body cavity (such as the abdomen) using an inert chemical (e.g., perfluorocarbon), independent of the lungs. The external circuit includes many components configured to control properties of the chemical, including temperature, flow rate, pressure, oxygenation percentage, carbon dioxide percentage, and such other properties as may be deemed appropriate in a particular implementation by those skilled in the art. The system also includes safety features to reduce the likelihood of injury to the patient. Each of the safety features and chemical properties can be controlled by a healthcare worker, such as a physician, nurse, or emergency operator, for a particular patient. In some cases, the system may have the potential to mitigate the ventilator-induced lung injury pathway and promote/accelerate lung healing. Furthermore, for some patients who have arrived at the limits of mechanical ventilator support, a pulmonary-independent method of oxygenation and decarboxylation might be their only hope to survive long enough for their lungs to recover. Thus, the system causes oxygenation perfusion in the abdomen with oxygenated perfluorocarbon and offers an effective pulmonary-independent system for augmenting gas exchange. In some cases, this technique could save lives during outbreaks of respiratory illnesses.

Perfluorocarbons ("PFC") are dense, colorless, nontoxic, inert, fluorine-based liquids with extraordinary gas dissolving properties, typically around 50 ml of oxygen and 200 ml of $CO_2$ per 100 ml of liquid at 37° C.

Previous work on PFC oxygenation remains incomplete in a number of important ways. First, the results of related experiments focus predominantly on quasi-equilibrium conditions. This makes it difficult to use the resulting datasets for the modeling and identification of the underlying transient dynamics. This, in turn, makes it difficult to utilize these results for closed-loop control system analysis and design. In a practical clinical setting, the well-recognized robustness benefits of closed-loop control are needed in order to achieve desirable oxygenation and carbon dioxide clearance rates in the presence of patient-to-patient variability.

Second, previous work focused predominantly on examining the oxygenation benefits of peritoneal oxygenated PFC circulation. For example, the "trigger" that launched each experiment was the achievement of a target initial state of hypoxia in the given test animal. Thus, such prior work has generally been limited in its potential to provide data that can be used for assessing the ability of peritoneal oxygenated PFC circulation to serve as a clearing mechanism for high $CO_2$ concentrations—the other component of pulmonary failure, along with low oxygen concentrations.

Finally, previous work has not measured the rate of oxygen or carbon dioxide transport through peritoneal oxygenated PFC circulation. For example, the list of measured experimental data did not include the concentration of $CO_2$ in the circulated PFC fluid or in the exhaust gas emanating from that fluid. Thus, there is a need for gas exchange through peritoneal oxygenated PFC circulation, that accounts for both $O_2$ and $CO_2$ transport/diffusion dynamics.

Systems and methods configured in accordance with certain aspects of the invention thus capitalize on the unique advantages of perfluorocarbons as facilitators for gas exchange. Such systems and methods as disclosed herein are radically different from traditional liquid ventilation, in that they involve circulating an oxygenated PFC through the abdomen (more specifically, the peritoneal cavity), as opposed to the lungs, using the peritoneal cavity is used for gas exchange. Specifically, such systems and methods as disclosed herein involve circulating (or perfusing) an oxygenated PFC through the abdominal cavity. Diffusion then allows oxygen and carbon dioxide to be exchanged between the oxygenated perfluorocarbon and the patient's bloodstream, thereby providing extra-pulmonary respiratory support. One advantage of this configuration is that it does not involve a direct blood-device interface, thereby avoiding many of the potential risks and contraindications of ECMO. Another advantage is that instead of attempting to wring more function out of injured lungs, as with liquid ventilation, systems and methods as disclosed herein help to rest the lungs and create potentially favorable conditions for their potential healing. Such systems and methods have the disruptive potential to revolutionize the field of respiratory support, thereby potentially helping to save thousands of patients' lives annually.

In order to assess the function of systems and methods configured in accordance with the invention, a system was developed for circulating PFC fluid from an oxygenating tank to a peritoneal cavity, and from the peritoneal cavity to a $CO_2$ removal tank with desired flow rate, pressure, and temperature. Such system was constructed for IACUC-approved experiments on large laboratory animals (i.e., pigs). The system contains actuation mechanisms such as bypass valves in order to provide functionalities such as the safe rerouting of fluid away from the animal in case of excessively high pressures and/or excessively high/low temperatures. The system was equipped with extensive data acquisition capabilities, the intent being to facilitate the detailed analysis of experimental results. Time-synchronized measurements were logged by this data acquisition (DAQ) system at a master rate of 100 samples/second.

In accordance with aspects of an embodiment of the invention, a system for peritoneal oxygenation is provided, comprising: a suction canister system having fluidly separated portions; a gas exchange system comprising a carbon dioxide removal tank and an oxygenation tank; a fluid delivery system fluidly connecting the gas exchanger with the suction canister system and having at least one cannula configured to couple the fluid delivery system to a patient's abdominal cavity; and multiple control algorithms intended for the closed-loop control of perfusate temperature, abdominal intra-cavity pressure, perfusion flowrate, dissolved gas concentrations in the perfusate (including both oxygen and $CO_2$ concentration), and—in one embodiment of the invention involving a dual-canister suction system—the automated switching between the use of active suction to drain perfluorocarbon into a suction canister and the use of a second canister to supply the drained liquid to the $CO_2$ removal chamber.

In accordance with other aspects of an embodiment of the invention, a method for peritoneal oxygenation is provided, comprising the steps of providing a system for peritoneal oxygenation, comprising (in one embodiment of the invention) a suction canister system having fluidly separated portions, a gas exchanger comprising a carbon dioxide removal tank and an oxygenation tank, a fluid delivery system fluidly communicating the gas exchanger with the suction canister system and having at least one cannula configured to fluidly couple the fluid delivery system to a patient's abdominal cavity, and a controller; and causing the system to alternate operation of each fluidly separated portion between suctioning oxygenation fluid from a patient's abdominal cavity and feeding oxygenation fluid to the gas exchanger.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
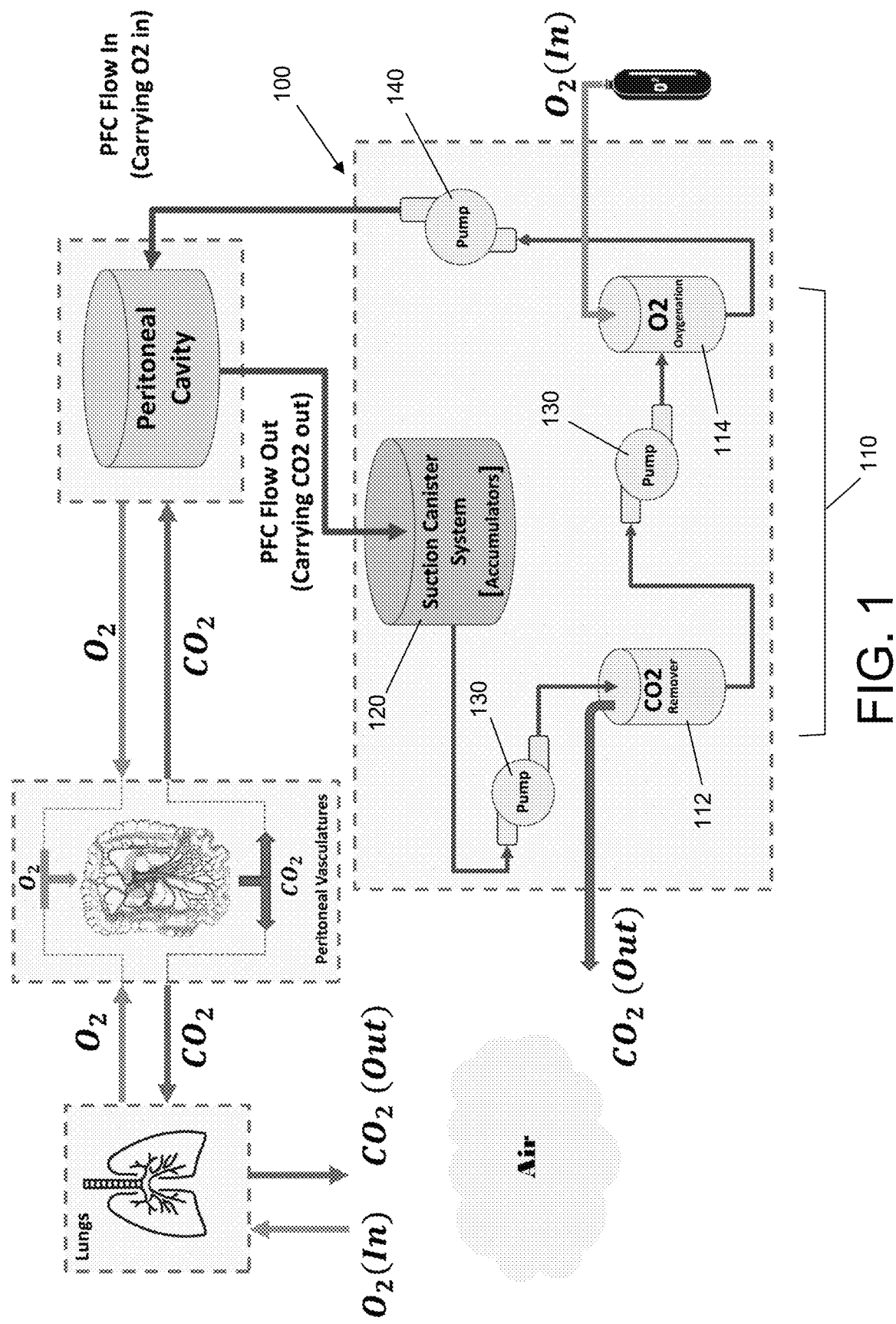
FIG. 1 is a schematic view of a system for body oxygenation and ventilation through perfusing PFC fluid to the peritoneal cavity in accordance with certain aspects of an embodiment of the invention.

FIG. 1 is a schematic view of a system 100 for body oxygenation and ventilation through perfusing PFC fluid to the peritoneal cavity in accordance with certain features of an embodiment of the invention. The system is configured to supplement gas exchange in a patient, and uses a fluid circuit to cause oxygenation perfusion in a patient's body cavity (such as abdomen) using an inert chemical fluid (e.g., PFC) independent of a patient's lungs. The fluid circuit includes many components configured to control properties of the fluid, including temperature, flow rate, pressure, oxygenation percentage, carbon dioxide percentage, and such other properties as may occur to those skilled in the art. The system causes oxygenation perfusion in the abdomen with oxygenated PFC as an effective pulmonary-independent system for augmenting gas exchange. In some cases, this technique could save lives during outbreaks of respiratory illnesses. This same perfusion system is not limited to use in the peritoneal cavity, but could also be used to circulate PFC, or some other gas carrying compound, through other areas in the body, such as the bladder, the stomach, the intestines, and/or the pleural space(s).

In certain configurations, system 100 includes a gas exchanger 110 configured to exchange an oxygenation gas for a waste gas from a fluid. For example, exchanger 110 perfuses oxygen ($O_2$) as the oxygenation gas into the fluid and decarboxylates (removes the waste gas carbon dioxide ($CO_2$)) from the fluid. The system 100 includes an output circuit that includes a reservoir system 120, at least one output pump 130, and tubing. In certain configurations, a sterilizer (not shown) may be provided, such as by way of non-limiting example positioned between the reservoir system 120 and the output pump 130. The gas exchanger 110 receives the fluid from the reservoir system 120 via the output pump 130. One possible operating principle for this sterilizer is the use of an ultraviolet floodlight for sterilization. In certain configurations, filters (not shown) may be included as part of the fluid flow pathway. The output circuit is configured to fluidly couple the patient to the gas exchanger 110, as further discussed below. The gas exchanger 110 removes a substantial portion of the $CO_2$ from the fluid such that perfusion of the fluid within a patient is unlikely to cause harm, according to typical medical standards. In certain configurations, the fluid has a desired ratio of $O_2$ to $CO_2$ when oxygenated and another ratio of $O_2$ to $CO_2$ when exhausted. Thus, the system is configured to produce an oxygenation gradient between the fluid when oxygenated and a patient's oxygen saturation.

In an exemplary configuration, gas exchanger 110 includes a waste portion 112 that is configured to remove $CO_2$ from the fluid using a wash fluid, such as air. Gas exchanger 110 may receive air at a controlled pressure, such as by way of non-limiting example at 50 PSI (e.g., controlled by a regulator) from a typical source (such as a wall or bottle air source). In such configuration, the air washes over the fluid having higher amounts of dissolved $CO_2$ to remove $CO_2$ (e.g., via a $CO_2$ gradient between the air and the fluid). For example, the fluid may be in gas-permeable tubing (or other container via a spray nozzle) through which $CO_2$ can be removed. The fluid may flow through the tubing at a flow rate and pressure controlled by a controller. The controller may also control the flow rate and pressure of the wash air or gas. In certain configurations, the sweep gas may be bubbled through the $CO_2$ removal chamber to remove $CO_2$ from the PFC. $CO_2$ removed from the fluid can then exhaust from the exchanger via a vent filter or one-way exhaust, such as a HEPA filter or the like. In certain configurations, the fluid may be heated or cooled (e.g., such as by a heater, condenser or the like) to a desired temperature to facilitate $CO_2$ removal. Likewise in certain configurations, $CO_2$ removed from the fluid may be compressed and removed from the circuit, such as a to a high-pressure gas tank, for disposal and thus avoid the expulsion of the exhaust into the patient's room. In this manner, gas exchanger 110 may be configured to remove $CO_2$ from the fluid.

Likewise and in accordance with further aspects of an embodiment, an oxygenation portion 114 of gas exchanger 110 may be separately configured from the waste portion 112. For example, the oxygenation portion 114 may comprise a separate component from the waste portion 112, which oxygenation portion 114 is fluidly coupled to the waste portion 112. In certain configurations, the system may be configured to remove $CO_2$ from the fluid using a scrubber. For example, the system can include a scrubber typically used in anesthesia circuits. As a further example, the scrubber can include a canister containing a substance that removes $CO_2$ from the fluid, such as soda lime. Likewise in certain configurations, the substance can be lithium hydroxide.

As mentioned above, system 100 may include a sterilizer such that gas exchanger 110 receives sterile fluid from the reservoir system 120. For example, the output circuit of system 100 may include a sterilizer that substantially kills microbes (e.g., bacteria, viruses, etc.) in the fluid that has been removed from the patient. In certain configurations, the sterilizer may comprise an ultraviolet (UV) light source configured to emit light into the fluid at a wavelength (i.e. UV-C) to kill microbes. In other configurations, the sterilizer may comprise a heater (e.g., infrared or heating source). In still other configurations, the sterilizer may comprise a combination of UV and heating sources. In still other configurations, the sterilizer may include a filter configured to remove microbes. In still other configurations, the sterilizer may include a skimmer configured to remove fluids (e.g., from the reservoir or circuit) of a density that is likely to contain microbes (e.g., removing perfusate from a bottom portion of the reservoir). Preferably, the output circuit is modular, such that individual components can be exchanged, repaired, and replaced without necessitating substantial change to other components.

As further mentioned above, gas exchanger 110 includes oxygenation portion 114 configured to oxygenate the fluid. In certain configurations, gas exchanger 110 receives oxygen in oxygenation portion 114 through a diffuser from an external supply, such as a wall or bottle source, having a pressure and flow rate that is controlled by an oxygen gas regulator. The diffuser perfuses the oxygen gas into the fluid. In certain configurations, the oxygen diffuses into the fluid through an oxygen micropore diffuser, or the like. Furthermore, the oxygenation portion 114 may be configured to heat the fluid, such as by a heater. In certain configurations, the heater may include a temperature sensor that is coupled to the controller. For example, the heater may be configured to control the temperature of the oxygenated fluid into the patient to substantially match the patient's body temperature. In certain configurations, the circuit is configured to reduce heat loss from the circuit, fluid, and tubing (e.g., when a relatively small amount of heating is needed). For example, the circuit may include insulation substantially surrounding the tubing, reservoir, and gas exchanger. Likewise in certain configurations, a heating element such as an electric heating element may heat the fluid to the desired temperature. In still further configurations, the system may include a heat exchanger to heat the fluid through heat transferred from another working fluid. For example, the working fluid can be typical working fluids, such as water, ethylene glycol, or the like. In this manner, the heater may be controlled by the controller using sensor feedback from the temperature sensor and other sensors.

Gas exchanger 110 is further fluidly coupled to a patient to transmit oxygenated fluid to the patient's peritoneal cavity. For example, oxygenated fluid is pumped from the oxygenation portion 114 or gas exchanger 110 to the patient through an input circuit. In certain configurations, the input circuit includes an input pump 140, at least one valve and sensors as discussed in greater detail below, and a bubble eliminator. In certain configurations, the input pump 140 may comprise a parallel pump, although other pumps may be used, such as by way of non-limiting example a roller pump, a peristaltic pump, or the like.

In certain configurations, the input circuit may optionally be further fluidly coupled to the waste portion 112 of the gas exchanger 110 via a return line. In such configuration, the return line may be configured to allow oxygenated fluid to flow from the input circuit to the waste portion 112 of the gas exchanger 110. For example, the return line can be fluidly coupled at a shunt valve in the input circuit configured to be controlled by the controller. Preferably, the input circuit is modular, such that individual components can be exchanged, repaired, and replaced without necessitating substantial change to other components.

Further, fluid flow (such as pressure, flow rate, and volume) in the return line can be controlled by the controller as discussed in greater detail below.

System 100 also preferably includes at least one cannula configured to fluidly couple the system to the patient. For example, a cannula that may be coupled to the input circuit is a 28F surgical cannula. In certain configurations, the cannula may include sensors configured to provide feedback from the cannula to the controller for controlling parameters of the system (e.g., $O_2$ flow rates, pressure, temperature, etc.) as described herein. For example, the cannula can include a pressure sensor configured to be positioned in the patient's abdominal cavity to measure pressure within the patient's abdominal cavity for controlling parameters of the system. In some cases, the parameters of the system are controlled such that the pressure, fluid temperature, $O_2$ concentration, and $CO_2$ concentration within the patient's abdominal cavity are maintained within a safety range for the patient. Likewise in an exemplary configuration, the patient's intraabdominal pressure as measured by a pressure sensor may enable closed-loop control of PFC flowrate in the system.

In certain configurations, system 100 may be configured to adjust operation of system parameters when the patient's parameters are outside of a safety range. For example, the system 100 may adjust fluid pressure, flow rates, and the like. A pressure within the patient's body, such as their abdominal cavity, that is outside of a safety range for the patient can be a trigger to automatically shut down the system 100. The trigger can also cause alerts (e.g., visual, audio, messaging, etc.) for healthcare workers. In certain configurations, system 100 may include a siphon drainage line configured to reduce pressure within the patient's abdominal cavity when the pressure is above a safety range. In certain configurations, increases in intracavity pressure measurement beyond a medical practitioner-determined safety limit may cause an automatic reduction in perfusion flowrate, or an automated increase in siphoning flowrate through the adjustment of siphoning-related parameters such as suction pressure, thereby bringing pressure back to a safe range in a controlled manner. In certain configurations, bladder pressure measurement is used as a safety trigger either as a proxy for, or in addition to, intracavity pressure measurement, and used to automatically trigger the onset of pressure safety control. Likewise in certain configurations, system 100 may include a pressure relief valve configured to reduce pressure within the patient's abdominal cavity when the pressure is above a safety range. In certain configurations, multiple passive and active pressure safety measures are implemented—including the use of mechanical pressure relief valves and software-based flow regulation—in a hierarchical manner.

As mentioned above, the oxygenation fluid employed in system 100 as described herein preferably comprises PFC, and in certain exemplary configurations may more particularly comprise perfluorodecalin. In certain configurations, the fluid may comprise a mixture of perfluorocarbons and other fluids. For example, the fluid can be APF-140HP, such as produced by FLUOROMED. APF-140HP is a controlled mixture of isomers of perfluorodecalin and other perfluorinated C10 compounds. APF-140HP is generally available as Cosmetic-Grade (external use only) and Research Grade (not suitable for use in humans except under an approved protocol and available in sterile or non-sterile filled containers). Perfluorodecalin is approximately twice the density of water and three times the kinematic viscosity of water (at room temperature). Thus, perfluorodecalin is approximately 6× the dynamic viscosity of water (at room temperature). Since the mechanical torque required for pumping fluid is generally a function of the fluid's dynamic viscosity, typical pumps, such as described above, are generally able to pump perfluorodecalin at given flow rates. As a further example, at standard atmospheric temperature and pressure, perfluorocarbons can dissolve approximately one ml of oxygen for every 4 ml of PFC fluid. Thus, on a volumetric basis, perfluorocarbons can have a solubility of approximately 25%.

PFCs used in systems and methods according to aspects of the invention may having the following physical characteristics:

| | |
|---|---|
| Boiling Range | 140-143° C. |
| Pour Point: | 0° C. |
| Liquid Density, 25° C.: | 1.93 g/ml |
| Vapor Density, (air = 1): | 16 |
| Vapor Pressure, 25° C.: | 6.25 torr |
| Thermal Conductivity, 25° C. | 0.58 cal/hr cm ° C. |
| Average Molecular Weight: | 462 |
| Heat of Vaporization: | 16.1 cal/g |
| Kinematic Viscosity, 25° C.: | 2.94 cSt |
| Surface Tension, 25° C.: | 19.3 dynes/cm |
| Coefficient of Expansion: | 0.0010 cm$^3$/cm$^3$ ° C. |
| Refractive Index, 25° C.: | 1.31* |
| Oxygen Solubility, 25° C.: | 49 ml O$_2$/100 ml |
| Dielectric Strength, 25° C.: | >33 kV (2.5 mm gap)* |
| Ozone Depletion Potential: | 0 (Relative to Freon 22) |

*Estimated Value

In certain configurations, the fluid in the system may comprise perfluorocarbon F44E (trans-bis-perfluorobutyle ethylene). F44E is a dense, colorless, nontoxic, inert liquid with gas dissolving properties, around 50 ml of oxygen and 200 ml of CO$_2$ per 100 ml of liquid at 37 Celsius.

System 100 preferably includes a controller that is configured to control various parameters of the system (such as described above). Furthermore, parameters of system 100 can be further controlled based on signals or feedback from sensors that measure physiological parameters of the patient. For example, the sensors can include pressure sensors positioned within the patient, such as positioned on a cannula (as mentioned above). The controller can further include a model configured to determine parameters of the system based on signals from the system. For example, the model can have a control algorithm or strategy, such as a linear quadratic regulator (LQR) control strategy. That model preferably includes model variables and model assumptions. Model variables may include input variables such as volumetric flowrate and inflow. Model variables may also include output variables such as volumetric flowrate and outflow. Model variables may still further include state variables such as a difference (delta) between desired and actual states (such as states of parameters of abdominal pressure, blood oxygen level, such as governed by single compartment model, etc.). In certain configurations, the model may include a plant model, which may have the exemplary form:

$$dx1/dt = k1(x1-x2)$$

$$dx2/dt = k2(x2) - k3(x1)$$

In an exemplary configuration, the controller may operate on a microcomputer. For example, the microcomputer can be configured to operate the model, such as described above. The controller may be configured to receive signals from various sensors of the system (for example, as inputs for the model). The controller may be further configured to determine parameters of the system according to the model or algorithm. Still further, the controller may be configured to output signals to various components of the system (e.g., sterilizer, pumps, gas exchanger, valves, heater, etc.) to affect parameters of the system (as described above). In an exemplary configuration, the controller may be wired locally to the patient, i.e., wired to the system's components. In other configurations, the controller may be located at a remote location, for example, on a server, remote computer or portable device. For example, the controller can be electrically connected to a local area network, the Internet, or a cloud service. Still further, the controller may be configured to integrate with external control devices, such as bedside monitors and the like. Still yet further, the controller may be integrated with typical medical software systems (e.g., EPIC, Cerner) to monitor and/or record patient data.

In an effort to confirm the feasibility and function of the foregoing model, a simple idealization of the hypothesized real CO$_2$ transport processes in the peritoneal cavity was developed. Such model comprises a control-oriented, multi-compartment model of the dynamics of CO$_2$ clearance through a system for peritoneal PFC circulation, such that system 100 may be configured to operate according to such model. The model's gray-box nature makes it possible to assign clear biological meanings (and, therefore, plausible ranges of values based on the systems biology literature) to most of the model parameters. Thus, the development of the model can be used in many cases, such as animal experiments. The datasets gathered through animal experiments can also be used for model parameterization, validation, and refinement. This includes refinements to the model's idealized mathematical representations of underlying diffusion dynamics, for instance.

The model can have a model description that is configured to consider the dynamics of both O$_2$ and CO$_2$ diffusion/transport, recognizing the coupling between these dynamics. The model captures the coupled dynamics of four compartments, namely: (i) the peritoneal cavity, (ii) lungs, (iii) capillary vasculature, and (iv) external PFC storage tank. The model comprises a nonlinear time-domain state-space model, with ten state variables, namely: (i) the volume of PFC fluid in the peritoneal cavity; (ii) lung volume; and (iii-x) the concentrations of both O$_2$ and CO$_2$ in all four compartments. Three exogenous disturbance inputs affect this model, namely: (i) the rate of change of lung volume with time due to breathing; (ii) the rate at which O$_2$ leaves the vasculature compartment to enable metabolism; and (iii) the rate at which CO$_2$ enters the vasculature compartment due to metabolism. Of these three disturbance inputs, only one is treated as a measurable disturbance, namely, the time rate of change of lung volume due to breathing. The model also has five control input variables, namely: (i) the volumetric flowrate of the PFC fluid into the peritoneal cavity; (ii-iii) $O_2/CO_2$ concentrations of the air supply to the lungs; (iv) the rate at which $O_2$ is added to the PFC fluid in the external storage tank; and (v) the rate at which $CO_2$ is expunged from the PFC fluid in the external storage tank. The model assumes these control inputs to be both measured and adjustable within reasonable bounds. For instance, the rate at which $CO_2$ is expunged from the PFC fluid in the external storage tank can be controlled, within limits, through actions such as heating the PFC fluid once it exits the peritoneal cavity. The volumetric flowrate of PFC fluid out of the peritoneal cavity will not be treated as a control input. Instead, it will be assumed to be driven by natural siphoning due to (i) gravity plus (ii) the difference in pressure between the peritoneal cavity and atmosphere. This assumption recognizes the inherent safety risks associated with the use of mechanical pumps to "siphon" the fluid out of the peritoneal cavity. Building the above state-space model involves the use of the following laws of physics. First, Fick's and Henry's laws are used for modeling species diffusion between the various biological compartments. Second, Bernoulli's equation is used for modeling the orifice flow of PFC out of the peritoneal cavity. Third, mass conservation laws, together with the pure integral relationship between lung volume and its time rate of change, are used for deriving state equations for the concentrations of $CO_2$ in the above compartments. Fourth, pressure buildup inside the peritoneal cavity is modeled using a linear elastic relationship between volumetric expansion and pressure.

Given the above preliminary dynamic model, system 100 may include sensors to make sure that key experimental variables are either directly measured or at least observable. The sensors may be configured to measure various parameters, such as: (i) peritoneal cavity pressure; (ii) PFC flowrate and $O_2/CO_2$ concentrations at the inlet and outlet of the peritoneal cavity; (iii) volumetric $O_2/CO_2$ gas concentrations and/or flowrates into and out of the external PFC fluid tank; (iv) quantities typically available from a mechanical ventilator (e.g., end-tidal $O_2/CO_2$ tension, minute ventilation, tidal volume, etc.); and (v) arterial/venous $O_2/CO_2$ concentrations (via blood sampling).

Testing of system 100 was conducted using an experimental protocol. Peritoneal profusion/circulation of oxygenated saline solution was used as a positive control case for all animal experiments. A number of healthy pigs were used in the experiments, and all experiments began with the adjustment of inhaled $O_2$ concentration to a value between 10% and 20% in order to render the pigs hypoxic. PFC infusion was triggered by the detection of a target value of either $O_2$ or $CO_2$ concentration in the animal's blood, reflecting the importance of studying both oxygenation and ventilation. Once PFC infusion is triggered, at least three different types of experiments can be conducted, such as: no-circulation experiments, constant circulation experiments, and time-varying circulation experiments. In a no-circulation experiment, the peritoneal cavity is filled with oxygenated PFC fluid until the cavity pressure is either (i) 800 Pa (6 mmHg) or (ii) 1333 Pa (10 mmHg). Damage to the cavity may be expected if the pressure exceeds 1600 Pa (12 mmHg). This fluid remains static in the peritoneal cavity, its release prevented by the closure of an outflow release valve. At the end of the experiment, the fluid is drained from the peritoneal cavity, then its $O_2/CO_2$ contents are measured and analyzed. Such an experiment is useful for evaluating the flowrate-independent diffusion of $O_2/CO_2$ into PFC liquid injected into the abdominal cavity, potentially at different pressure levels. In a constant circulation experiment, oxygenated PFC is circulated through the peritoneal cavity at a constant volumetric rate of inflow.

Several factors can be varied between different constant circulation experiments, one being the rate of PFC fluid inflow into the abdominal cavity. For example, PFC fluid inflow can have values between 1 l/min and 4 l/min. Other factors that can be varied between constant circulation experiments include the rates of $O_2$ insertion and $CO_2$ removal from the external PFC fluid storage tank, as well as the percent inhaled oxygen. Finally, in a variable circulation experiment, key input variables such as the volumetric rate of PFC inflow into the abdomen are adjusted dynamically, for example, as either sequences of step functions or as sinusoidal functions of time. Thus, variable circulation experiments can be used for system identification to estimate parameters and dynamic model validation. Thus, an experimental plan can include a variety of no-, constant-, and variable-circulation tests to determine many variations of underlying parameters (e.g., PFC flowrate, PFC oxygenation level, initial hypoxia level, etc.).

An exemplary embodiment of the system is discussed above. In certain configurations, the system includes parameters of a $CO_2$ clearance model. For example, the parameters of the $CO_2$ clearance model can include estimated model parameters that are biologically plausible for patients. The parameters of the $CO_2$ clearance model can be determined by iterating mathematical modeling/system identification trials until the estimated model parameters become biologically plausible and/or the autocorrelation of the model's residuals suggests that they are sufficiently close to being correct. Thus, the system will include a simple, biologically plausible, experimentally-validated, control-oriented, multi-compartment model of the dynamics of swine $CO_2$ clearance through the peritoneal circulation of oxygenated PFC fluid for autonomous closed-loop control of oxygenated peritoneal PFC circulation.

Figure 2:
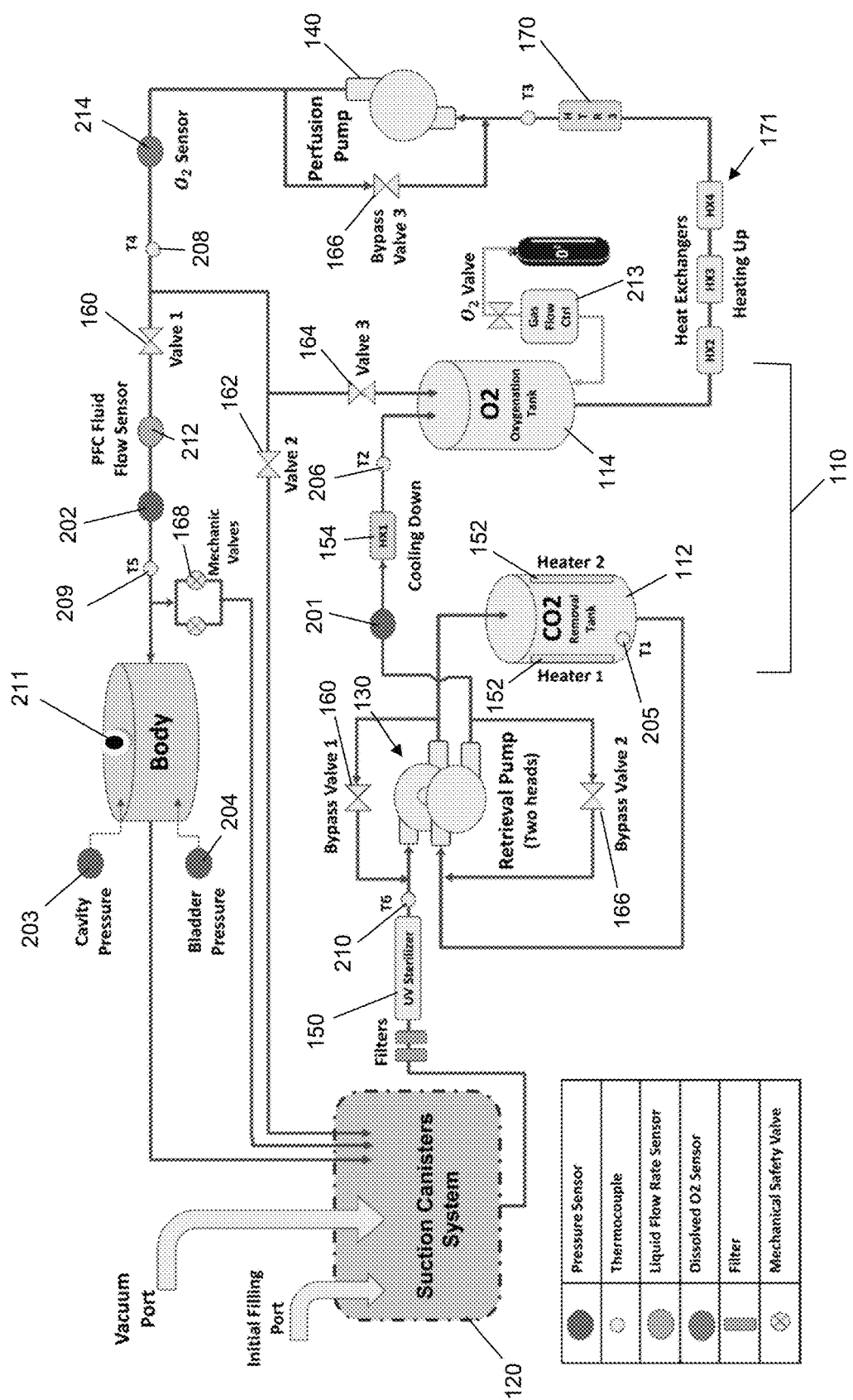
FIG. 2 is a schematic view of the system of FIG. 1 including a detailed view of system actuators and sensors.
Figure 3:
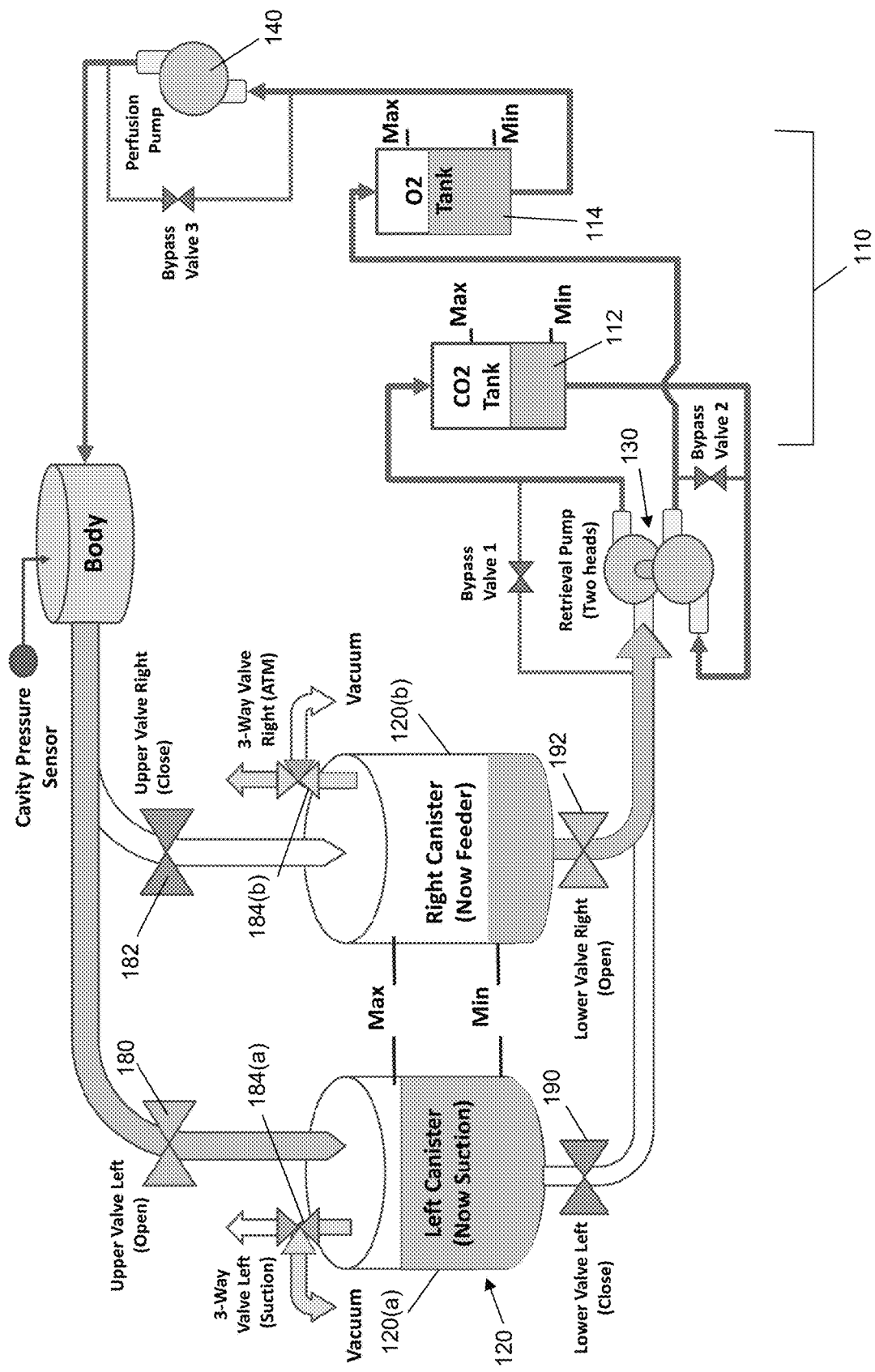
FIG. 3 is a schematic view of the system of FIG. 1 including a detailed view of a dual suction canister system in accordance with certain aspects of an embodiment of the invention.

Next, FIG. 2 is a more detailed schematic view of system 100 including the ventilation configuration, sensors, and actuators, and FIG. 3 is a schematic view of system 100 showing further details of the flow system and particularly the multi-canister configuration of reservoir system 120. As shown in FIGS. 2 and 3, PFC fluid leaves the patient's peritoneal cavity through active suction into one or more external canisters 120(*a*) and 120(*b*) of reservoir system 120, such as suction canisters. Once the PFC is in the system, it: (i) is sanitized at sterilizer 150, such as an ultraviolet flood light; (ii) passes through $CO_2$ removal chamber 112 where carbon dioxide purging is facilitated by heating up the liquid (such as via heaters 152); (iii) is then cooled back down via a heat exchanger 154 to improve the next task of the setup which is oxygenation; (iv) gets oxygenated at oxygenation portion 114, which may comprise a dedicated bubble chamber; and (v) is perfused back through the patient's peritoneal cavity via a pump 140, such as a peristaltic perfusion pump. As shown in FIG. 2, the system includes additional actuation mechanisms such as bypass valves in order to provide functionalities such as the safe rerouting of fluid away from the patient in case of excessively high flow pressures and also high/low temperatures. As noted above, outlet pumps 130 (each comprising, by way of example, a peristaltic retrieval pump) are provided for draining the PFC fluid from reservoir system 120 to the $CO_2$ tank 112, and for draining the PFC fluid from the $CO_2$ tank 112 to the $O_2$ tank. A vacuum pump (not shown) may be fluidly attached to each suction canister 120(*a*) and 120(*b*) or reservoir system 120 for suctioning PFC fluid from the patient to the reservoir system. A first solenoid valve 160 provides for PFC fluid perfusion to the patient's body. A second solenoid valve 162 provides for bypassing the patient's body and sending the PFC to reservoir system 120. A third solenoid valve 164 may be provided for transferring PFC fluid directly to oxygenation chamber 114. Bypass solenoid valves 166 are preferably provided for recirculation of PFC through outlet pumps 130 and inlet pump 140. Mechanical valves 168 may also be provided to prevent high pressure PFC fluid from going into the patient's body. Heaters 152 are preferably provided on $CO_2$ removal tank 112 for increasing the fluid temperature inside of $CO_2$ removal tank 112 up to 50° C., and a final heater 170 is provided for increasing the PFC fluid temperature before perfusing to the patient's body, up to 39° C.

As particularly shown in FIG. 3 and discussed in greater detail below, first/left suction canister 120(a) includes an upper first canister valve 180 providing an on/off function for flowing PFC fluid from the patient to first/left suction canister 120(a), and second/right suction canister 120(b) includes an upper second canister valve 182 providing an on/off function for flow PFC fluid from the patient to second/right suction canister 120(b). Likewise, each of suction canisters 120(a) and 120(b) may include a 3-way valve 184(a) and 184(b), respectively, for switching function between negative versus atmospheric pressure on the suction canisters 120(a) and 120(b), as discussed in greater detail below.

With continued reference to FIGS. 2 and 3, system 100 includes a number of sensors that collect various pressure, temperature, gas level, and flow rates in the system, which data is used as input to the controller to maintain intended operational parameters for system 100, as further discussed below. More particularly, a first pressure sensor 201 is positioned between pumps 130 and oxygenation tank 114, a second pressure sensor 202 is positioned before perfusing PFC into the patient's body, a third pressure sensor 203 is positioned inside of the patient's abdominal cavity, and a further pressure sensor 204 is positioned inside of the patient's bladder. Further, various thermocouples are provided, including a first thermocouple 205 positioned to measure the temperature of $CO_2$ removal tank 112, a second thermocouple 206 positioned to measure the temperature of the PFC fluid at the inlet to the $O_2$ chamber 114, a third thermocouple 207 positioned to measure the temperature of the PFC fluid at the inlet to the perfusion pump 140, a fourth thermocouple 208 positioned before bypass valve 162 to confirm a safe PFC temperature for the patient's body, a fifth thermocouple 209 positioned to measure the actual body inlet temperature, a sixth thermocouple 210 positioned to measure PFC temperature at the inlet to the $CO_2$ removal chamber 112, and a seventh thermocouple 211 positioned to measure the patient's body surface temperature. Fluid level sensors (not shown) are provided in each of first and second suction canisters 120(a) and 120(b). A PFC fluid flow rate sensor 212 is provided to measure PFC fluid flow rate immediately prior to perfusing into the patient's body. Likewise, a gas mass flow sensor 213 is positioned to measure the inlet $O_2$ gas flow rate into oxygenation tank 114. Finally, a dissolved oxygen sensor 214 is provided on the inlet flow line before perfusing PFC fluid into the patient's body to measure PFC fluid oxygen percentage, which dissolved oxygen sensor 214 measures the percentage of oxygen carried by the PFC liquid into the patient's abdomen and may be used as data input to the controller to adjust gas delivery to the system.

Heating of the PFC fluid has been found to be an important factor in the successful implementation of a system and method for peritoneal oxygenation as described herein. The fluid temperature before perfusing to the animal's peritoneal cavity should be close to the animal's body temperature. Moreover, the PFC stored in the $CO_2$ tank should have a higher temperature than the animal's body temperature in order to expedite the $CO_2$ removal. As shown in FIG. 2, there are three heat supplies at three different locations in system 100. The two heaters 152 in $CO_2$ removal tank 112 preferably provide a heating rate of 500 W together, and the heater 170 located before the perfusion pump 140 generates heat at a rate of 100 W. Moreover, an external cardioplegia heater-chiller unit 171 may supply a heating capacity of approximately 3000 W via the three heat exchangers located after the oxygenation tank 114. In other words, these heaters are dispensing more than the theoretical amount of energy required to heat the PFC fluid up to our desired points in this configuration. Given the thermal losses along the tubes and across the canisters, the heaters should provide enough heat to maintain an appropriate animal body temperature at the outlet of the setup and in the $CO_2$ removal tank. The external cardioplegia heater unit may be operated at 41° C. (max) for warming, and its chiller circuit at 20° C. for cooling the PFC fluid which flows into the oxygenating tank 114. The flow rates of the PFC going through the heating and cooling stages of this external unit will be identical, since their individual pump heads (the two heads of retrieval pump 130) are preferably driven by the same motor.

In an exemplary configuration, the capacity of system 100 was designed to be 23 liters before starting the perfusion, and the system 100 delivered about 10-11 liters of PFC into the animal's body during circulation.

With the foregoing combination of sensors and actuators, in combination with time-synchronized physiological data collected from medical equipment including an anesthesia machine, pulse oximeter, and capnography monitor, a rich data acquisition configuration results that may, in turn, enable closed-loop control of system 100. Thus, closed-loop feedback controllers provide automated temperature and pressure control in system 100, including for maintaining the temperature of the $CO_2$ removal chamber at desire set point temperatures, and for maintaining the temperature of the perfused PFC fluid near (+/−0.5° C.) the patient's temperature.

Next and with continuing reference to FIG. 3, the controller of system 100 employs sequential discrete-event switching logic for the valves of the suction canister system 120, and for the perfusion pump and retrieval pump bypass valves to maintain smooth circulation of the PFC fluid while allowing continuous PFC fluid drainage from the patient's peritoneal cavity. The dual suction canister configuration shown in FIG. 3 is particularly provided to avoid a potential problem with negative back pressure that could limit the system to address higher flow rates with the system pumps. The dual suction canister system shown in FIG. 3 ensures that atmospheric pressure is always present in the canister that is feeding the system 100 (the right/second canister 120(b) in the view of FIG. 3). This configuration also provides negative pressure in the canister into which the PFC is being drained (the left/first canister 120(a) in the view of FIG. 3). Based on the volume of the PFC in these two suction canisters 120(a) and 120(b), the controller switches the upper (180 and 182), lower (190 and 192), and 3-way valves (184(a) and 184(b)) to switch the first/left 120(a) and second/right 120(b) suction canister's function from suction to feeder and vice versa.

More particularly, when either one of first suction canister 120(a) or second suction canister 120(b) has been drained and its associated bottom valve 190 and 192, respectively, is open, the controller reduces flowrate through the retrieval pumps 130 to zero. Likewise, when the first/left suction canister 120(a) reaches a maximum PFC fluid level (as show in FIG. 3), the controller carries out a transition process to transition the current suction canister 120(a) to feed, and the current feed canister 120(b) to suction. To carry out that process, the controller carries out the following steps:

(i) The flowrate of PFC through the retrieval pumps 130 is reduced to zero, and the system optionally pauses for a short duration (e.g., 1 second).

(ii) The first lower valve 190 is closed, and the system optionally pauses for a short duration (e.g., 1 second).

(iii) Each 3-way valve 184(a) and 184(b) is set to vent each suction canister 120(a) and 120(b) to atmosphere, the valve 184(b) of suction canister 120(b) is now set to the vacuum/negative pressure position so that it may take over as the suction canister, and the system optionally pauses for a short duration (e.g., 3 seconds).

(iv) First upper valve 180 is then closed, second upper valve 182 is opened, the atmospheric vents on each of suction canisters 120(a) and 120(b) are closed, the system optionally pauses for a short duration (e.g., 1 second).

(v) The 3-way valve 184(a) of first suction canister 120(a) is now set to the positive pressure position so that it may take over as the feeder canister, and the system optionally pauses for a short duration (e.g., 1 second).

(vi) The second/right lower valve 192 is closed to seal the second suction canister 120(b) (again which now will serve as the suction canister), and the system optionally pauses for a short duration (e.g., 1 second).

(vii) The first lower valve 190 is then opened to enable feeding PFC into the system, and the system optionally pauses for a short duration (e.g., 1 second).

(viii) Finally, the retrieval pumps 130 are engaged at the desired flow rate to now receive PFC from the first canister 120(a) while the second canister 120(b) now suctions additional PFC from the patient's body.

The foregoing process is particularly configured to ensure that the following safety principles are employed: (i) the PFC should always be continuously drained from the patient, and PFC back flow into the animal should be avoided; (ii) the PFC fluid should never be pulled using pumps 130 through a pair of closed bottom valves 190 and 192; (iii) if the left and right canisters 120(a) and 120(b) are both empty, pumps 130 should have zero flow; (iv) we should avoid attempting to pump against a negative air pressure; and (v) the canisters 120(a) and 1209b) should not be over filled. The retrieval pump flow rate and its bypass valves along the suction canisters system's valves are adjusted by the controller in order to maintain the above safety principles. In an exemplary configuration, the designed discrete-event control algorithms may be implemented using the "Switch Case" blocks in Simulink.

Figure 4:
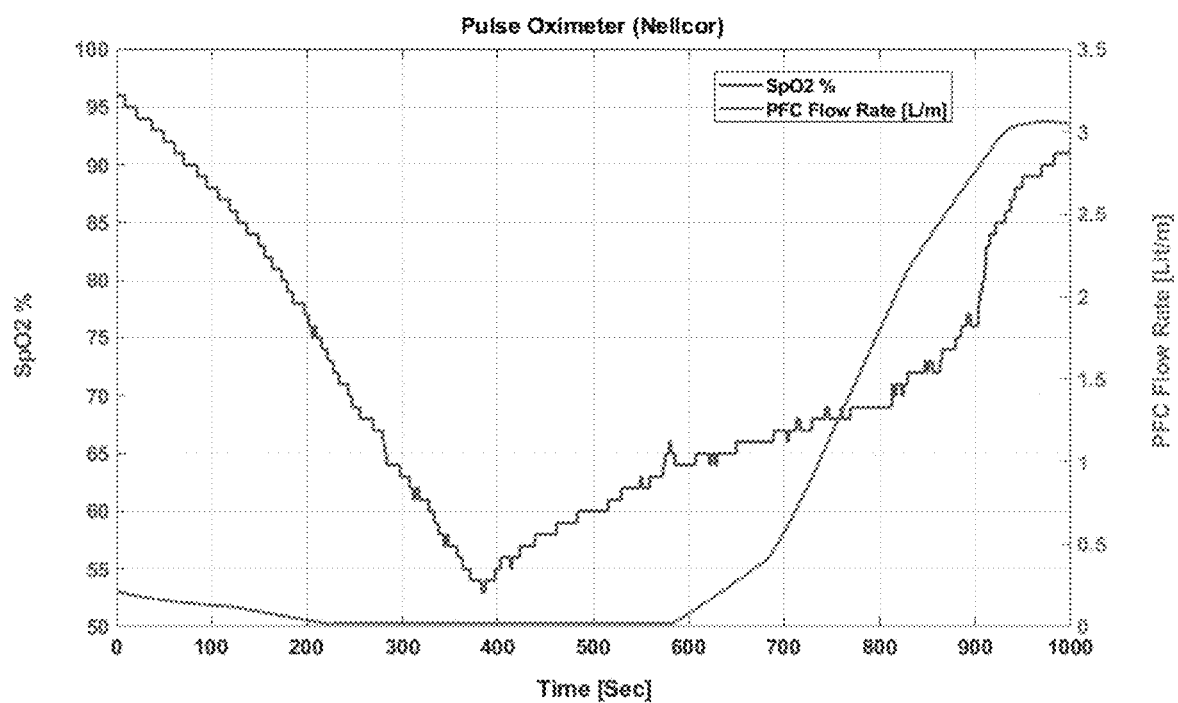
FIG. 4 is a graph showing blood oxygen concentration $SpO_2$ and its change corresponding to change in PFC perfusion flow rate in a test animal using a system and method in accordance with aspects of the invention.

In an experimental implementation of the foregoing system and method, it was established that such system and method are capable of monitoring key physical variables pertaining to the state of the test animal. For instance, the system 100 is capable of monitoring quantities such as peritoneal intra-cavity pressure. A key insight from those experiments is that systems and methods configured in accordance with aspects of the invention are capable of oxygenating the test animal's blood. The most encouraging evidence for the success of the second animal experiment is shown in FIG. 4. $SpO_2$, also known as oxygen saturation, is a measure of the amount of oxygen-carrying hemoglobin in the blood relative to the amount of hemoglobin not carrying oxygen. Normal $SpO_2$ is about 95%; however, in this experiment the pig's blood oxygen saturation is deliberately decreased to almost 55% to investigate the impact of extracorporeal oxygenation through the novel ventilator setup. FIG. 4 shows a remarkable improvement in $SpO_2$ from 65% to 90% during the time interval of 600 to 1000 seconds. The jump in $SpO_2$ at time 400 seconds is because of a slight manual increase in $FiO_2$ in the anesthesia machine.

Figure 5:
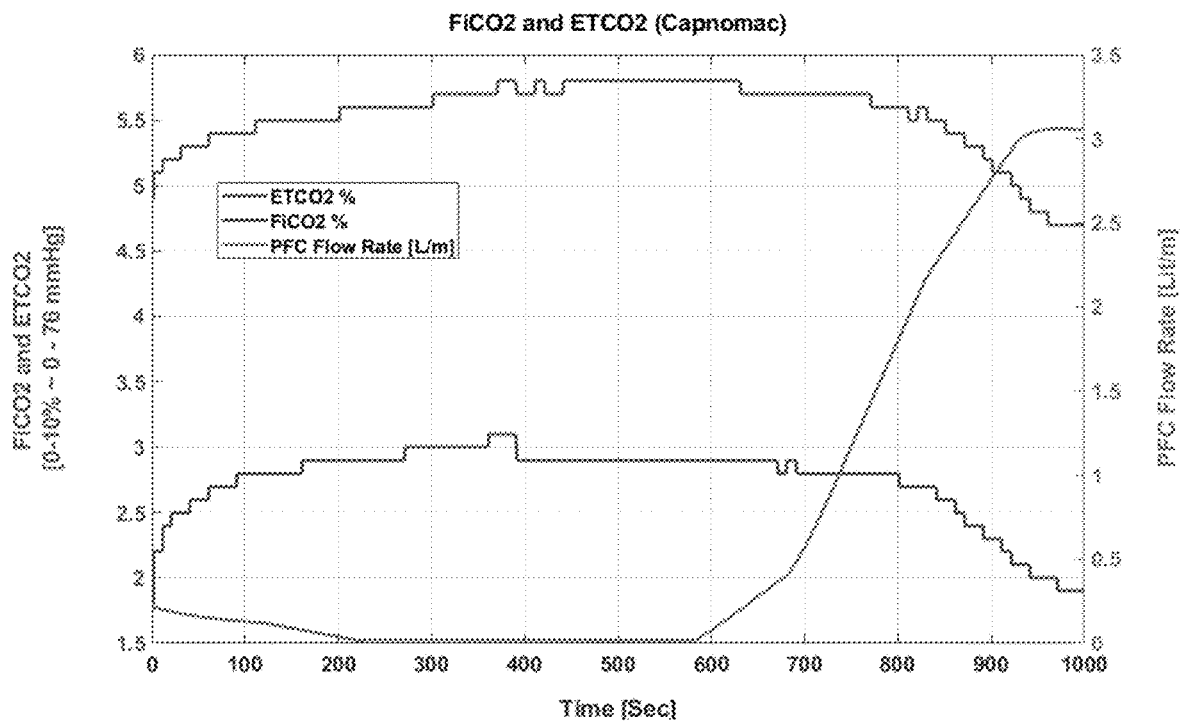
FIG. 5 is a graph showing respiratory $FiCO_2$ and end tidal $ETCO_2$ records and their changes corresponding to change in PFC perfusion flow rate in a test animal using a system and method in accordance with aspects of the invention.

Another key insight is that systems and methods configured in accordance with aspects of the invention can, in addition to oxygenation, also assist with carbon dioxide removal from the test animal's bloodstream. FIG. 5 shows a window of 1000 seconds of data acquisition for respiratory $CO_2$ "($FiCO_2$)" and end tidal $CO_2$ during on and off PFC perfusion. This data is from the second animal experiment. During the animal experiment the fully oxygenated PFC perfuses to the pig's peritoneal cavity with the rate of at most 3.2 liters per minute. The unit of $ETCO_2$ and $FiCO_2$ in this figure is "%" (0 to 10%, which corresponds to 0 to 76 mmHg). The anesthetized pig's $ETCO_2$ is changing from 4% to 10% (from 30.4 mmHg to 76 mmHg). This figure suggests that there is indeed a potentially linear relationship between $CO_2$ clearance and PFC perfusion flow rate. During the time 600-900 seconds, the PFC perfusion flow rate increases from 0-3 L/min, and at the same time interval both the $FiCO_2$ and $ETCO_2$ percentages decrease. The apposite behavior is traceable at the time window of 0-200 seconds. This is a very promising result showing a successful experiment in removing $CO_2$ from the pig's blood stream during PFC fluid circulation through the pig's peritoneal cavity.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

What is claimed is:

1. A system for peritoneal oxygenation, the system comprising:
    a suction canister system having fluidly separated portions;
    a gas exchanger comprising a carbon dioxide removal tank and an oxygenation tank;
    wherein said gas exchanger is in fluid communication with said suction canister system and is configured for fluid coupling to a patient's abdominal cavity; and
    a controller configured to cause each of said fluidly separated portions to alternate between suctioning an oxygenation fluid from the patient's abdominal cavity and feeding the oxygenation fluid to the gas exchanger.

2. The system for peritoneal oxygenation of claim 1, wherein each of said fluidly separated portions comprises one of a plurality of fluid canisters, wherein a first one of said fluid canisters has a first inlet valve and a first outlet valve, and wherein a second one of said fluid canisters has a second inlet valve and a second outlet valve.

3. The system for peritoneal oxygenation of claim 2, wherein said controller is further configured to position said first inlet valve open when said second inlet valve is closed, and wherein said controller is further configured to position said second inlet valve open when said first inlet valve is closed.

4. The system for peritoneal oxygenation of claim 3, wherein said controller is further configured to position said first outlet valve closed when said first inlet valve is open, and wherein said controller is further configured to position said second outlet valve open when said second inlet valve is closed.

5. The system for peritoneal oxygenation of claim 3, wherein each of said fluid canisters further comprises a valve configured to vent to atmosphere.

6. The system for peritoneal oxygenation of claim 3, wherein each of said fluid canisters further comprises a valve configured to fluidly connect each of said fluid canisters to a vacuum source.

7. The system for peritoneal oxygenation of claim 1, wherein said controller is further configured to transition a first one of said fluidly separated portions from suctioning said oxygenation fluid from the patient's abdominal cavity to feeding of said oxygenation fluid that has been suctioned to said gas exchanger upon said oxygenation fluid that has been suctioned reaching a predesignated maximum fill level in said first one of said fluidly separated portions.

8. The system for peritoneal oxygenation of claim 7, wherein said controller is further configured to simultaneously transition a second one of said fluidly separated portions from feeding said oxygenation fluid to suctioning said oxygenation fluid upon transitioning said first one of said fluidly separated portions from suctioning said oxygenation fluid to feeding said oxygenation fluid.

9. The system for peritoneal oxygenation of claim 1, further comprising a pump between and in fluid communication with each of said suction canister system and said gas exchanger.

10. The system for peritoneal oxygenation of claim 9, wherein said controller is further configured to set a flow rate of said pump to zero upon either a first one of said fluidly separated portions or a second one of said fluidly separated portions having an oxygenation fluid level below a predetermined minimum level.

11. A method for peritoneal oxygenation, the method comprising:
providing a system for the peritoneal oxygenation, the system comprising:
a suction canister system having fluidly separated portions;
a gas exchanger comprising a carbon dioxide removal tank and an oxygenation tank;
wherein said gas exchanger is in fluid communication with said suction canister system and is configured for fluid coupling to a patient's abdominal cavity; and
a controller; and
causing said system to alternate operation of each of said fluidly separated portions between suctioning an oxygenation fluid from the patient's abdominal cavity and feeding said oxygenation fluid to the gas exchanger.

12. The method for peritoneal oxygenation of claim 11, further comprising controlling a temperature of said oxygenation fluid at a point of perfusion into said patient to substantially match a body temperature of the patient.

13. The method for peritoneal oxygenation of claim 12, further comprising heating said oxygenation fluid in said carbon dioxide removal tank to a second temperature above said body temperature of said patient, wherein said second temperature is selected to increase carbon dioxide removal in said carbon dioxide removal tank.

14. The method for peritoneal oxygenation of claim 11, wherein each of said fluidly separated portions comprises one of a plurality of fluid canisters, wherein a first one of said fluid canisters has a first inlet valve and a first outlet valve, and wherein a second one of said fluid canisters has a second inlet valve and a second outlet valve.

15. The method for peritoneal oxygenation of claim 14, further comprising steps of positioning said first inlet valve open when said second inlet valve is closed, and positioning said second inlet valve open when said first inlet valve is closed.

16. The method for peritoneal oxygenation of claim 15, further comprising steps of positioning said first outlet valve closed when said first inlet valve is open, and positioning said second outlet valve open when said second inlet valve is closed.

17. The method for peritoneal oxygenation of claim 15, wherein each of said fluid canisters further comprises a valve configured to vent to atmosphere.

18. The method for peritoneal oxygenation of claim 15, wherein each of said fluid canisters further comprises a valve configured to fluidly connect each of said fluid canisters to a vacuum source.

19. The method for peritoneal oxygenation of claim 11, further comprising a step of transitioning a first one of said fluidly separated portions from suctioning said oxygenation fluid from the patient's abdominal cavity to feeding of said oxygenation fluid that has been suctioned to said gas exchanger upon said oxygenation fluid that has been suctioned reaching a predesignated maximum fill level in said first one of said fluidly separated portions.

20. The method for peritoneal oxygenation of claim 19, further comprising a step of simultaneously transitioning a second one of said fluidly separated portions from feeding said oxygenation fluid to suctioning said oxygenation fluid upon transitioning said first one of said fluidly separated portions from suctioning said oxygenation fluid to feeding said oxygenation fluid.

* * * * *